United States Patent
Heinrich et al.

(10) Patent No.: US 8,771,513 B2
(45) Date of Patent: Jul. 8, 2014

(54) REGENERATABLE FILTER FOR EXTRACORPORAL TREATMENT OF LIQUIDS CONTAINING PARTICLES AND USE THEREOF

(75) Inventors: Hans-Werner Heinrich, Griefswald (DE); Peter Kruschke, Griefswald (DE)

(73) Assignee: Adexter GmbH, Rostock (DE)

( * ) Notice: Subject to any disclaimer, the term of this patent is extended or adjusted under 35 U.S.C. 154(b) by 866 days.

(21) Appl. No.: 12/282,407

(22) PCT Filed: Mar. 14, 2007

(86) PCT No.: PCT/DE2007/000476
§ 371 (c)(1),
(2), (4) Date: Nov. 12, 2008

(87) PCT Pub. No.: WO2007/104298
PCT Pub. Date: Sep. 20, 2007

(65) Prior Publication Data
US 2011/0094962 A1     Apr. 28, 2011

(30) Foreign Application Priority Data

Mar. 14, 2006   (DE) .................. 10 2006 012 024

(51) Int. Cl.
*B01D 63/02*   (2006.01)
*B01D 15/08*   (2006.01)
*B01D 61/14*   (2006.01)

(52) U.S. Cl.
USPC .............. 210/321.9; 210/500.23; 210/321.88; 210/645; 210/636; 210/638; 210/289

(58) Field of Classification Search
None
See application file for complete search history.

(56) References Cited

U.S. PATENT DOCUMENTS

| 4,266,026 A | * | 5/1981 | Breslau ........................ 435/99 |
| 4,938,931 A | * | 7/1990 | Cussler ....................... 422/211 |
| 5,679,231 A | | 10/1997 | Alexander et al. |
| 6,497,675 B1 | | 12/2002 | Davankov |
| 6,866,783 B2 | * | 3/2005 | Baurmeister et al. ......... 210/649 |
| 2004/0220508 A1 | | 11/2004 | Strahilevitz |

FOREIGN PATENT DOCUMENTS

EP            0 139 949 A1     5/1985

OTHER PUBLICATIONS

International Search Report dated Sep. 9, 2007.

* cited by examiner

*Primary Examiner* — Krishnan S Menon
(74) *Attorney, Agent, or Firm* — Buchanan Ingersoll & Rooney PC (57) ABSTRACT

The invention relates to a regeneratable filtering and adsorbing system, combining the properties of membrane filtration with those of particle-based adsorption in a closed housing.

9 Claims, 5 Drawing Sheets

REGENERATABLE FILTER FOR EXTRACORPORAL TREATMENT OF LIQUIDS CONTAINING PARTICLES AND USE THEREOF

The invention relates to a regeneratable filter for extracorporal treatment of liquids containing particles and use thereof. The field of application of the invention is medicine, in particular direct blood treatment.

STATE OF SCIENCE

Alongside supporting influence on the healing of diseases, substances containing effective medications have been administered for millennia. A further possibility of therapeutic influence is the removal of noxious substances from blood by extracorporal treatment. The starting point for this development is the classical blood-letting, which was a standard therapy for certain diseases for more than two thousand years. New materials and technologies as well as the knowledge from blood group research made the introduction of haemodialysis in clinical application possible more than 50 years ago and led to blood exchange therapy, which was later replaced by plasma exchange. Low specificity, high costs and the risk of infection limit the application of plasma exchange.

Haemofiltration, haemodiafiltration, double filtration and plasma adsorption are milestones in the application of extracorporal therapy methods (or also therapeutic aphaeresis). With plasma adsorption, materials larger than albumin were removed from the blood for the first time. Unspecific or specific factors are used for the binding of highly molecular substances in the flowing blood or plasma.

As a result of electrostatic or hydrophobic interactions between the matrix and the component parts of the blood, LDL, beta2 microglobulin, endotoxins, immunoglobulins and circulating immune complexes are nowadays removed from the blood as a routine.

The specific affinity of protein A to the Fc receptor of IgG made the development of immuno-adsorbers possible, these being used, for example, for the depletion of IgG for treatment of severe forms of rheumatoid arthritis (Prosorba®).

Specific recognition sequences (antibodies, peptides) make removal of target structures with unambiguously defined specificity from blood possible. They are used, inter alia, for elimination of LDL (Therasorb®, LDL Lipopak®), Lp(a), (Lp(a) Lipopak®), acetylcholine receptor antibodies (MedisorbaMG®), anti-β1 adrenergic antibodies (Corafin®) or inflammation mediators (EP 1163004).

The use of the patients' own, dissociated immune complex components as ligands for a patent-specific immuno-adsorber (DE 19538641) is a special form on the path to increasingly purposeful and personalised therapy.

In all continuous aphaeresis methods, blood is continuously taken from a peripheral vein or a central venous catheter by means of a blood pump in an extracorporal circulation, mainly with a blood flow of 60-120 ml/min and re-transfused after removal of the pathogens via a different peripheral vein. Provision of this intermittently available extracorporal blood circulation is subject to similar conditions to extracorporal haemodialysis.

In most aphaeresis methods, a primary separation of plasma and blood cells before the actual plasma treatment is necessary. This primary separation can be done both by means of centrifugation plasma separation and also by means of filtration plasma separation. In both methods, pros and cons are equally to be taken into account. Essentially, filtration plasma separation is less complicated in handling and leads to a plasma free of thrombocytes. The disadvantage is the formation of a secondary membrane in the plasma filter, which limits the time of the effectivity of the filtration. On the other hand, a practically unlimited amount of plasma can be gained by centrifugation plasma separation without interruption. The slight contamination of thrombocytes can have a detrimental effect on the secondary separation.

As a rule, the filtrate flow is about 30% of the blood flow (plasma flow approx. 20-30 ml/min) in primary separation. Depending on the indication, once or twice the volume of plasma of the patient is normally treated. In treatment of one or two patient plasma volume(s) (assumption of a mono-compartmental model without re-distribution, synthesis or catabolism), a maximum reduction of the pathogen to 37% or 14% of the initial value can theoretically be achieved. However, these figures are mainly not reached in practice.

Unselective Plasmaphaeresis (Plasma Exchange)

In unselective plasma exchange, the plasma is separated from the blood cells in the extracorporal circulation with the help of a membrane plasma separator or a centrifuge, the entire plasma is rejected and substituted isovolaemically by an electrolyte solution plus human albumin or fresh plasma. The substitution solution is combined with the separated blood cells and re-infused into the patient. The benefit of the unselected plasma exchange is the simple set-up of the extracorporal circulation, the general applicability of the method for all pathogens accessible to aphaeresis, the effectivity in a pathogen structure which is not precisely known (e.g. in acetylcholine receptor antibody-negative Myasthenia gravis) and the relatively low extracorporal volume. The disadvantages are the immunoglobulin and coagulation factor depletion, the risk of intolerability of the substituted outside protein and a hyperoncotic substitution as well as the potential risk of infection in the transmission of pathogens with the substitution solution.

For the latter named reasons, unselective plasma exchange is nowadays only used if no selective method is available (e.g. in TTT, chylomicronaemia, antibody-negative Myasthenia gravis).

Membrane plasma separators comprise hollow-fibre modules with synthetic membranes (e.g. polyethylene or polysulfon). The surface is between 0.2 and 0.5 $m^2$, the pore size 0.2-0.5 μm. To monitor the extracorporal circulation, devices developed specifically for this purpose are used; as an alternative, use of devices for haemoperfusion or haemofiltration is also possible.

Selective Plasmaphaeresis

In selective plasmaphaeresis, the pathogen is removed from the plasma separated via a plasma filter (primary separation) in a secondary circulation, either by a further filtration process (secondary separation) or by adsorption (immunological or physicochemical) or by precipitation and the cleansed plasma is returned to the patient. Selective plasmaphaeresis requires specific devices, which monitor both the extracorporal blood circulation as well as the secondary circulation.

Double Filtration (Cascade Filtration, Membrane Differential Filtration)

This method uses a second filter with a smaller pore size (cut-off 25-40 nm) in a secondary circulation following separation of the plasma. The objective is to regain albumin as quantitatively as possible, on the other hand to retain the more highly molecular pathogenic protein in the secondary filter, which works in the so-called "dead-end" mode (occlusion of the distal discharge of the hollow fibres). As this method separates according to molecule size (molecular weight and spatial molecule conformation), it is only suited to removal of high-molecular pathogens such as IgM, fibrinogen or a-2-macroglobulin. Indications are therefore, for example, hyperviscosity syndrome, Morbus Waldenström, kryoglobulinaemia and hypercholesterinaemia. The use of double filtration plasmaphaeresis for treatment of microcirculation disorders is termed as rheophaeresis.

The benefits of this method compared with unselective plasma exchange are that no substitution solution is necessary and that selective removal particularly of the rheologically active proteins is possible, without disorders of the haemostasis coming about. The disadvantages are the limited capacity of the secondary filter as a result of possible blockage of the hollow fibres in very high initial figures as well as possible losses of immunoglobulin, which vary depending on the method.

Immuno-adsorption

Immuno-adsorption clinically means the binding of immunologically active molecules, for example to immobilised amino acids, peptides or proteins. The methods based on adsorption remove either certain classes of proteins or specifically a pathogenic antibody. In process engineering, vice versa, LDL binding to anti-apoprotein B-antibodies is referred to as LDL immuno-adsorption.

Elimination of Lipoproteins

The Liposorber® system (Kaneka, Osaka; Hospal, Planegg) is based on adsorption of LDL and Lp(a) from the plasma to dextrane sulphate/cellulose (DSC). The mechanism is based on an electrostatic interaction of the negatively charged sulphate groups of the dextrane sulphate with the positively charged Apo B of the two aforementioned lipoproteins. HDL, immunoglobulins and albumin are only adsorbed to a slight extent.

In the HELP® aphaeresis (heparin-induced extracorporal LDL precipitation, disposable product, Braun, Melsungen), LDL, Lp(a) and fibrinogen are precipitated from the plasma in the extracorporal circulation with an acid pH of 5.12 by means of heparin and are filtered off.

Elimination of Immunoglobulins

Immunosorba® system (Fresenius HemoCare, St. Wendel) uses staphylococci-protein-A as a ligand with Sepharose as a carrier.

Prosorba® system (Fresenius HemoCare, St. Wendel) uses staphylococci-protein-A as a ligand with a silica matrix as a carrier.

In Globaffin® (Fresenius HemoCare, St. Wendel), the synthetic peptide-GAM® as a ligand is immobilised on Sepharose CL-4B. The binding properties correspond to those of protein A.

Coraffin® (Fresenius HemoCare, St. Wendel) specifically removes auto-antibodies against the β1-adrenergic receptor of the cardiac muscle. This is an indication-specific method.

In the Ig-Therasorb® methods (Mitlenyi Biotec, Teterow), polyclonal anti-human-immunoglobulin sheep antibodies are immobilised on Sepharose CL-4B.

The Immusorba® system (ASAHI/Diamed, Cologne) works with non-reusable adsorbers on the basis of tryptophan (TR-350L) or phenyl alanine ligands (PH-350L), which are bound to a polyvinyl ethanol gel matrix.

Kryofiltration

In kryofiltration (Asahi Medical, Tokyo; Diamed, Cologne), the separated plasma is cooled to 4° C. for precipitation of kryoglobulines in a membrane-differential filtration process and, after separation of the precipitates, re-infused with the help of a kryofilter following heating up to body temperature.

Full Blood Aphaeresis

In full blood aphaeresis, noxious substances in the extracorporal circulation are removed directly from the blood more or less selectively with the help of adsorbing substances (activated carbon, exchanger resins) which are in a granulated form in an adsorber cartridge. It is similar to activated carbon haemoperfusion, which is used in intensive medicine for a series of intoxications. The size of the adsorber cartridge must guarantee a sufficient exchange surface and contact time of the adsorbent.

Direct adsorption of LDL and Lp(a) from full blood is made possible by the DALI® system (direct adsorption of lipoproteins of the firm of Fresenius HemoCare, St. Wendel). The adsorption cartridges for single use comprise negatively charged polyacrylate ligands, which have been immobilised on polyacrylamide and bind the atherogenic lipoproteins by electrostatic means.

Method, filtration and adsorption can be combined in varying ways. Matson et al. (U.S. Pat. No. 6,287,516) described a haemofiltration system comprising a blood filter with a downstream adsorber. The ultrafiltrate from the filter (exclusion MW # 50,000 Dalton) is pumped into an adsorber unit via a hose system, where the sepsis mediators are bound. The ultrafiltrate treated in this way can be combined with the primarily filtered blood through a further pump/hose/valve system and re-infused into the patient.

The advantage of specific adsorption is obvious, as only the (pathogenic) target substances are removed, without a negative influence on standard regulation by unspecific adsorption of "healing" plasma components. The disadvantage of all specific adsorption methods is that the ligands used, mainly specific antibodies, make the product expensive. This means a load on the overall treatment costs, in particular in diseases which have to be treated for a number of days or weeks. In EP 0139949, a device for blood cleansing is described, containing both the plasma filtering hollow fibres in a housing and also an adsorption matrix in the plasma area. A very similar device is described by Shettigar (WO 93/02777). Both have in common that the adsorbing matrix cannot be regenerated. The possibility of regeneration is expressly provided for in U.S. Pat. No. 6,497,675B1. The disadvantage here is that, although the adsorber unit is integrated into the plasma filter, it has to be removed from the housing for this purpose. This manipulation makes the process more complicated and increases the risk of confusion and thus the risk of transmission of diseases. The regenerated adsorber unit is screwed into a new plasma filter housing in a further work step.

SOLUTION ACCORDING TO THE INVENTION

What is desirable is the combination of the advantages of membranes (do not emit any particles, pore size can be chosen freely, favourably priced) with those of the particles (large possibilities of variations with a view to material classes, size, surface, activation and coupling of ligands) in one housing, which both permits the regeneration of the expensive functionalised particles and simultaneously frees the insides of the plasma filter membranes from bio-film, which customarily limits the usability of the membranes.

The objective of the invention is a full blood treatment unit which is marked by a simple system set-up, for example by doing away with pumps and additional hose connections, and combines the benefits of membranes and particles. The full blood treatment unit according to the invention is to make higher blood flows (up to 160 ml/min) possible, curtail the treatment time and, above all, be regeneratable.

Figure 1:
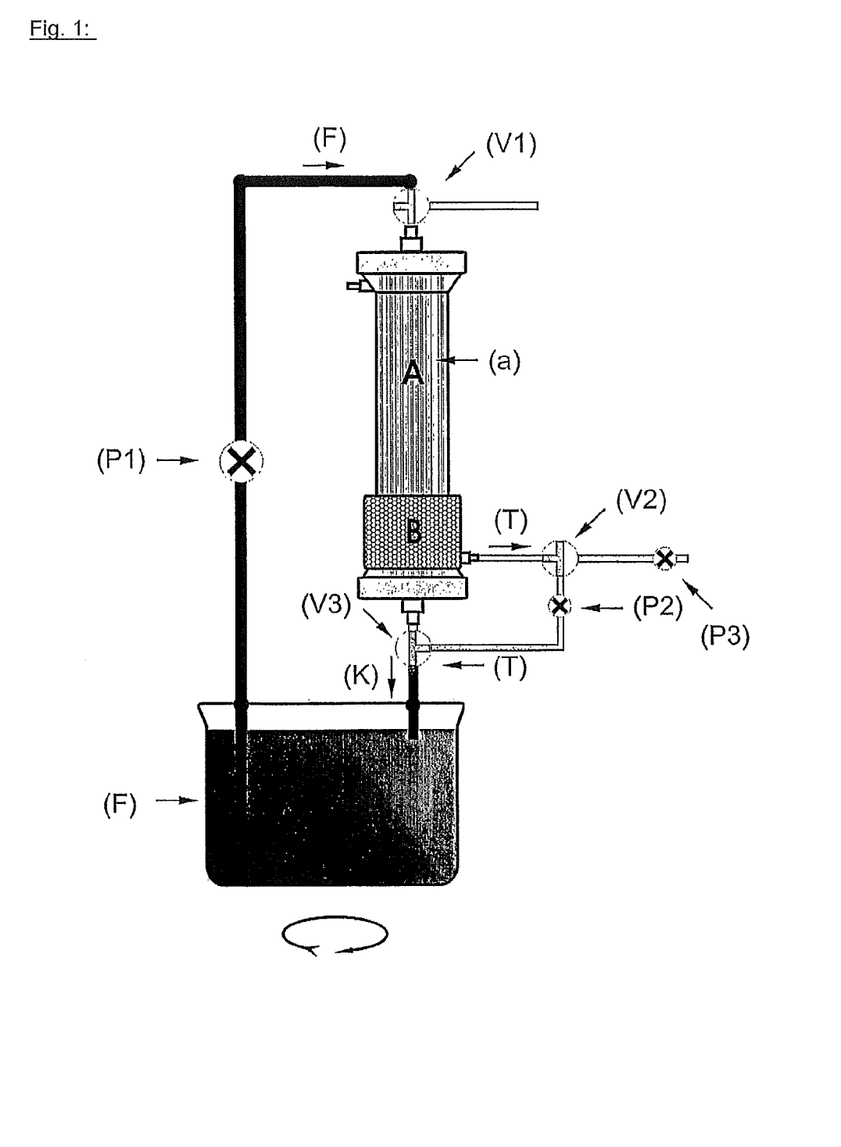
Figure 1A:
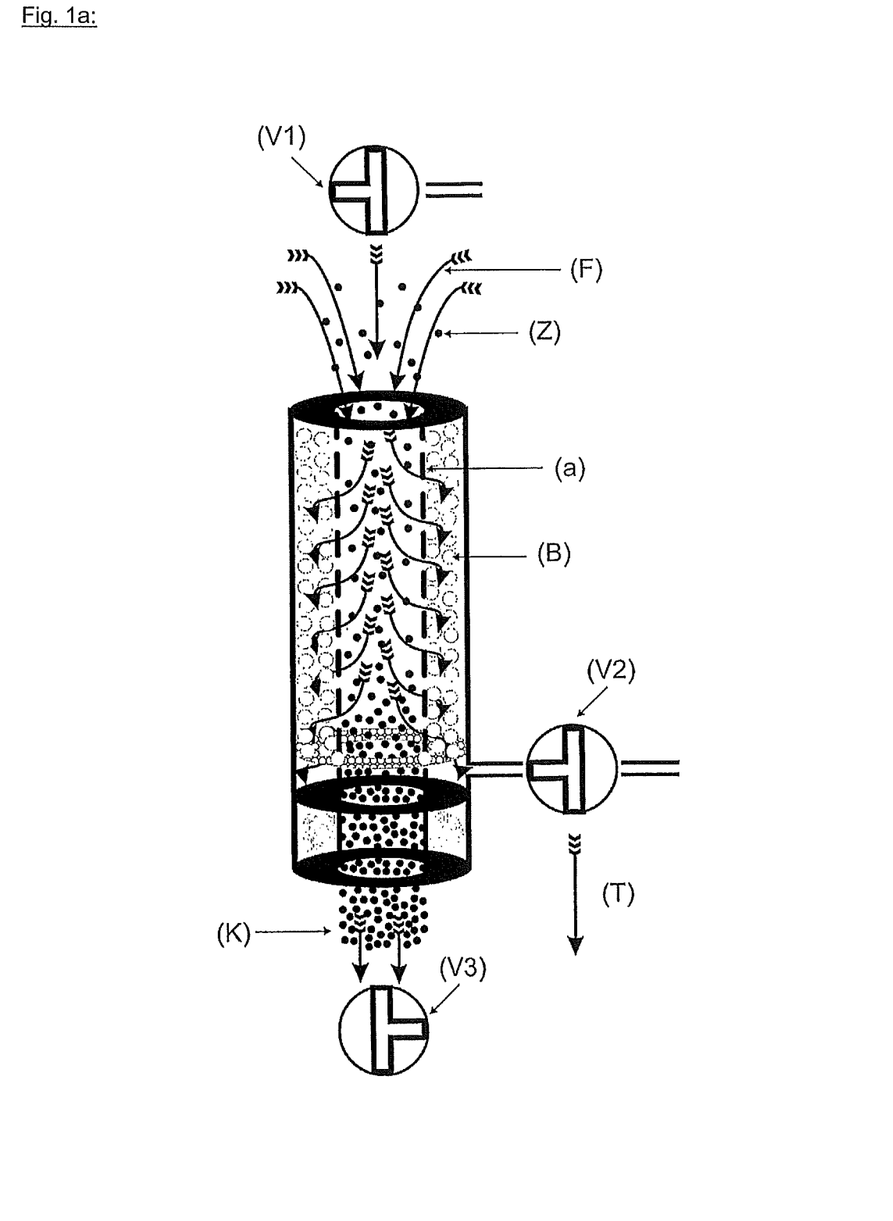

The objective is achieved by the fact that customary plasma filters (membrane hollow tubes) with the customary pore diameter of 0.2-0.5 μm are inserted in a housing of biocompatible material which is enclosed in itself (see FIG. 1 and FIG. 1a). Cellulose derivatives or synthetic materials such as polysulfons or polyamides can be used as the membrane material. The housing simultaneously acts as a container for the functionalised particles. For example, polysulfon, polyacrlyonitril, polymethyl methacylate, polyvinyl alcohol, polyamides, polycarbonates and cellulose derivatives can be used as the material for the particles. Inserted into the flowing blood, the plasma passes the membrane as a function of the pressure gradient and the pore size. Outside the membrane, the plasma now flows through the adsorber gel, comprising unspecifically or specifically functionalised micro-particles with a diameter above the pore diameter of the membrane. The plasma specifically cleaned of certain bioactive substances in this way is combined with the intra-luminal plasma filter blood flow in the housing and re-infused into the patient as cleansed full blood. A system of filters prevents micro-particles from entering the blood flow.

Figure 2:
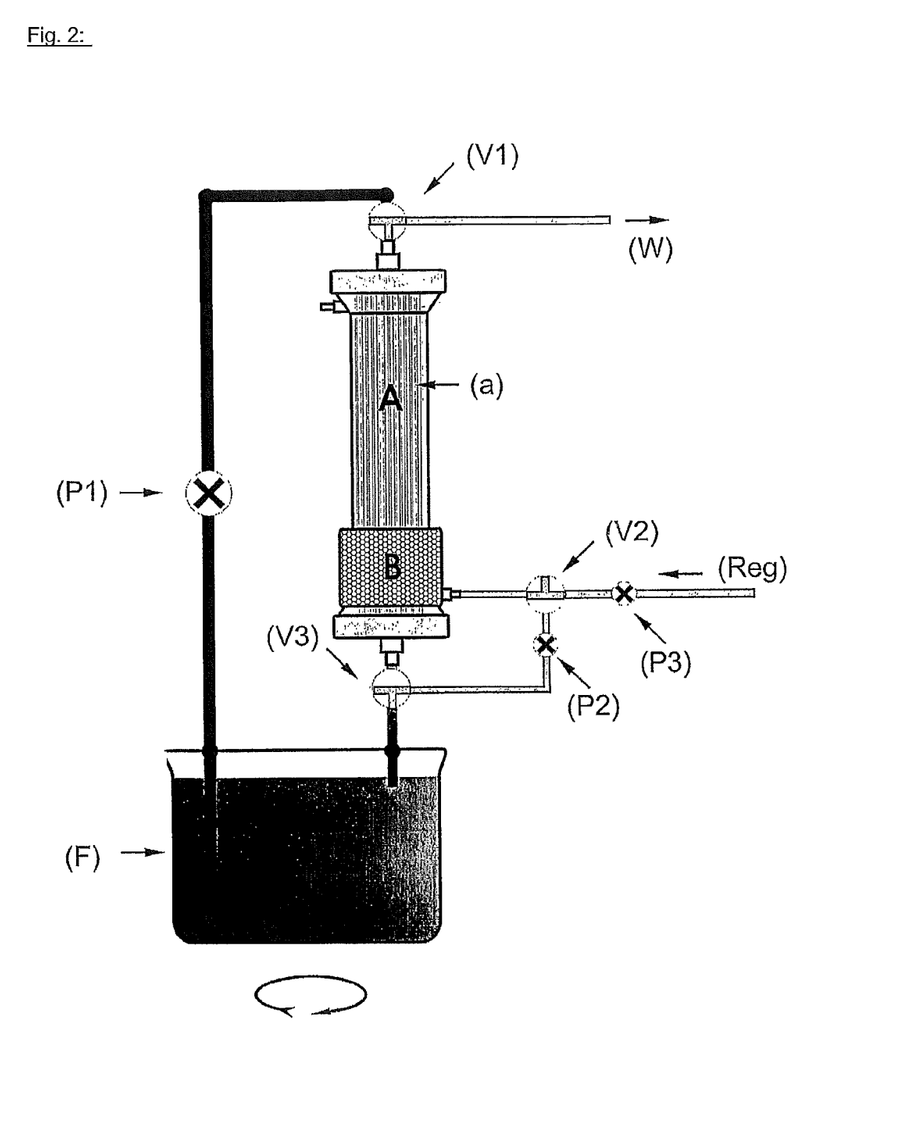
Figure 2A:
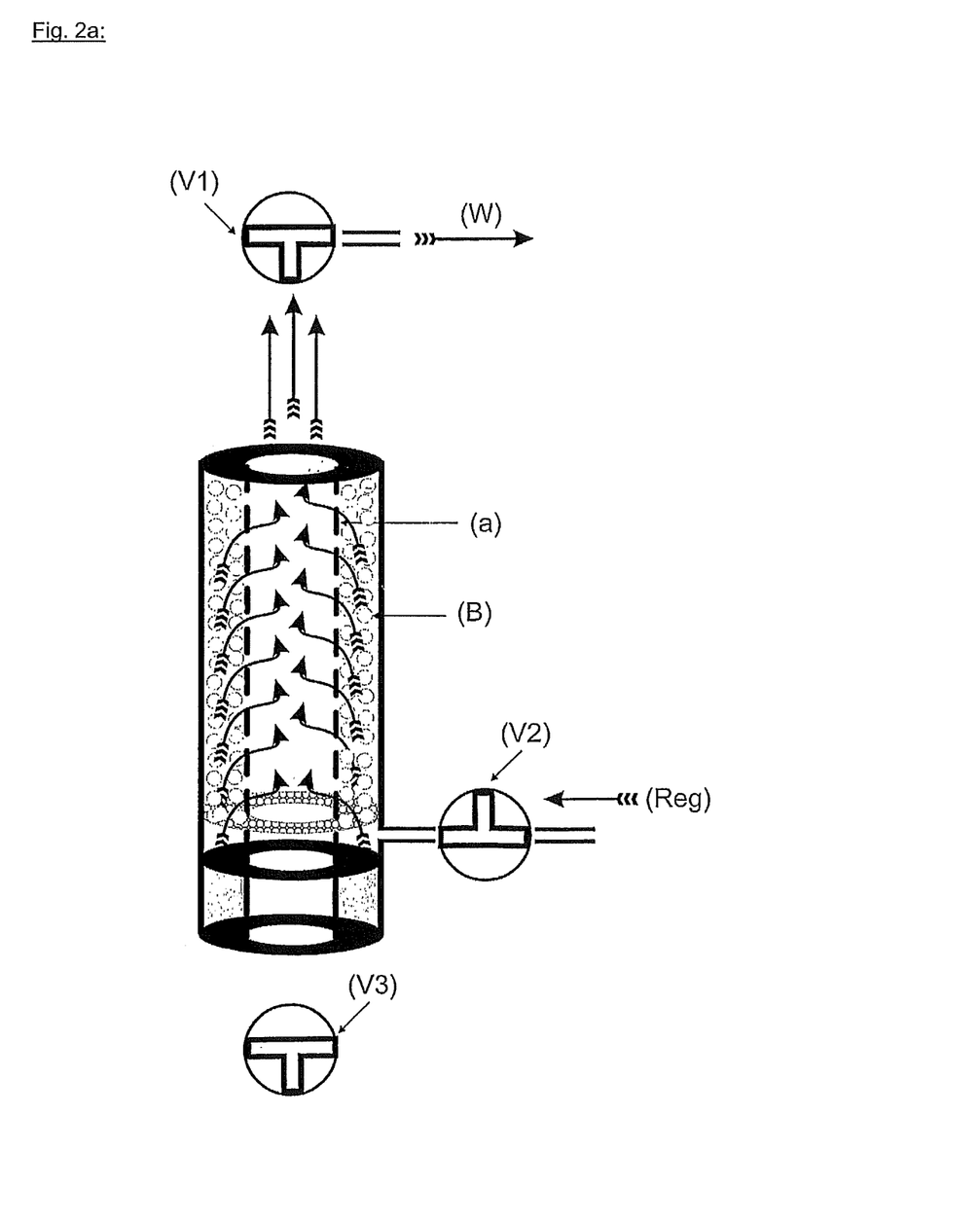

An essential feature of the invention is the fact that three-directional valves have been arranged in the filter system in such a way that pumping liquids into the particle area and flowing off from the entrance opening is made possible (see FIG. 2 and FIG. 2a). Through operation of these three-directional valves, the blood/plasma flow is stopped in the outlet of the housing after the adsorption potential has been exhausted. Regeneration is via the particle reservoir with customary buffers. The regeneration buffer enters the inside of the lumen of the filter membrane via the pores of the plasma filter and frees the surface of bio-film, with the result that the filter is available for the next treatment cycle following the expiry of the scavenging programme in question. According to the invention, the treatment system can also comprise two or more filters, with the result that treatment can be continued with one adsorber unit while the other one is being regenerated and a continuous blood treatment can take place in this way. The arrangement of the three-directional valves according to the invention makes regeneration of the functionalised particles possible for the first time without the adsorber unit having to be removed from the housing. In this way, the regeneration step can be done more quickly and with less technical effort. This is above all of great significance as confusion of the adsorber units of various patients is ruled out. This advantage ought in particular to be of great importance for routine operation in hospitals. In addition, the use of the device according to the invention does not harbour the risk of penetration of contaminations into the adsorber unit during replacement.

To sum up, it is seen that the therapy costs can be distinctly lowered by the use of the devices according to the invention in comparison with disposable products which demand extracorporal treatment lasting a number of days.

The invention is to be explained in more detail below by examples of embodiments.

Embodiment 1
Material and Methods 3 l of citrate blood of bovine origin were mixed with 1.5 μg recombinant human IL6 and pumped via the device shown in FIG. 1 in an enclosed circulation (parameters, see below).

The experimentally used device for the removal of antigens from full blood comprises a hollow-fibre plasma separator (A), the lower housing part of which has been replaced by an inserted cylinder (B), in which the adsorber gel surrounds the hollow fibres. The blood plasma released by the trans-membrane pressure has to pass the adsorber and is freed from the target substances in so doing.

The plasma separation module comprised a 0.4 m² hollow-fibre filter (A).

The adsorber container contained 60 ml of Sepharose, to which 5 mg IgY (vitelline antibodies from chickens' eggs, inoculated with IL6) were co-valently bound per ml of Sepharose.

The biding capacity of the adsorber amounted to 72 μg IL6.

The blood flow rate was set to about 120 ml/min.

A plasma flow of 20-25 ml/min was achieved in this.

After a plasma throughflow of 1.5 l all told, the adsorption was ended and the IL6 concentration in the blood determined (human-IL6-ELISA, Milenia Biotec).

Results:

The module can be operated without any problems.

The amount of plasma treated was 1.5 l.

Haemolysis was not observed.

The initial IL6 concentration of 500 pg/ml was lowered to 200 pg/ml during the 60 min duration of the adsorption. This corresponds to a depletion of 60% with a single passage of the total plasma volume through the adsorber in accordance with the device shown in FIG. 1 (see also FIG. 1a).

Embodiment 2
Activation of Sepharose 4FF and Coupling of Specific Anti-IL6 Antibodies
Material and Methods Solution A: 10 g cyanogen bromide (CNBr) was dissolved in 100 ml of acetone Solution B: 15.2 g of triethylamine was dissolved in 100 ml of acetone Solution C: 300 ml of acetone and 700 ml of $H_2O$ were mixed Solution D: 600 ml of acetone and 400 ml of $H_2O$ were mixed Buffer A: 0.5 M NaCl in 0.2 M carbonate buffer, pH 8.5

Buffer B: 0.5 M NaCl in 0.1 M acetate buffer, pH 4.5

Buffer C: PBS pH 7.4

Sepharose 4FF (Amersham/GE)

50 mg of vitelline antibodies (IgY), specific against human IL-6, dissolved in PBS, pH 8.5

Implementation:

Activation of the Sepharose 4FF according to the cyano-transfer method (Kohn J and Wilchek M. The use of cyanogen bromide and other novel cyanylating agents for the activation of polysaccharide resins. Appl Biochem Biotechnol. 1984;9:285-305). 15 ml of the Sepharose in 20% ethanol are taken from the original container and washed on a fine-particle filter with water (10×20 ml).

After this, there is washing 5× with 3:7 acetone and after than 5× with 6:4 acetone.

The sucked-off Sepharose is transferred to a suitable vessel and suspended in 8 ml of 6:4 acetone.

The suspension is agitated at −20° C. (10 min).

Then, 2 ml of CNBr solution are added, homogenised and 2 ml of TEA solution dripped in The mixture is sucked off on the fine-particle filter and washed with ice water.

After this, there is the determination of the activation according to (Kohn J, Wilchek M. A colorimetric method for monitoring activation of Sepharose by cyanogen bromide. Biochem Biophys Res Commun. 1978;84(1):7-14), by the concentration of the cynatester groups on the Sepharose being determined.

The activated Sepharose, which has been sucked dry, is stirred into the IgY solution and shaken for 2 hours at room temperature.

After this, the mixture is sucked off on the fine-particle filter and washed twice with buffer A, diluted 1:1 with $H_2O$. The solutions are collected and the protein content determined by measurement of the UV adsorption at 280 nm.

The gel is then subjected to repeated washing with the buffers in the order A, C, B. The loading of the Sepharose with IgY is then determined in a modified micro BCA method. The control is done via UV protein measurement of the washing liquids.

Results:

| Activation of the Sepharose | 9.8 µM/g moist Sepharose |
|---|---|
| Protein loading | 9.5 mg IgY/g moist Sepharose |

Embodiment 3
Production of a Full Blood Treatment Unit
1. Production of a housing to contain customary plasma filtration membranes (0.3 m²) of hollow fibres and 20 ml with anti-IL-6 functionalised adsorber particles (Sepharose 4FF).
2. Insertion of the bundle of membranes and casting of both openings to form an air-tight connection with the housing. The protruding ends of the hollow-fibre membranes are cut off.
3. Closure of both ends with caps, which carry the connecting branch.
4. The upper connecting branch is given a three-directional valve (V1), which serves the blood flow or the discharge of regenerate.
5. The lower lateral branch is provided with a three-directional valve (V2), which serves the discharge of the treated plasma or the incoming flow of regeneration and washing solutions.
6. The lower connecting branch is given the three-directional valve (V3) which serves to bring the treated plasma together with the corpuscular blood components to form treated full blood and, after it has been closed, prevents penetration of regeneration liquids into the full blood.
7. Pouring the functionalised Sepharose in via the lateral filling connection on the column body. Venting is done via the second lateral connecting branch.

Embodiment 4
In vitro Depletion of IL6 from Blood
Material and methods:
  Sepharose 4 FF (Amersham/GE), coupled after CNBr activation with vitelline antibodies (IgY) obtained from the egg yolk of chickens inoculated with human IL-6
  Coupling density: 5 mg IgY/ml packed Sepharose
  Recombinant human IL-6 (R&D Systems GmbH)
  Heparinised full blood
  IL6-ELISA kit (Milenia Biotec)
Implementation:
  In three different mixtures, 2 ml of full blood of a healthy person are spiked with 146 ng recombinant IL-6 in each case
  0.1 ml of IgY-Sepharose, specific against human IL-6, was added to the blood samples
The samples were moved on a shaker at room temperature. The IL-6 content of the blood was determined by means of ELISA as a function of time.

Results:
In batch experiments with IL6 (FIG. 3), it was proven reproducibly that Sepharose, loaded with anti-IL-6-IgY (5 mg/ml), is in the position to bind IL6 from the full blood. The quantity of IL-6 used roughly corresponds to that occurring in the blood of seriously ill patients, for example with severe sepsis and septic shock.

DESCRIPTIONS OF THE ILLUSTRATIONS

FIG. 1: Adsorption
The liquid (F) containing particles conveyed through the pump (P1) enters the device AB via a three-directional valve (V1), which is in the ⊣∥ position. As a result of the transmembrane pressure built up in the passage of the hollow fibres (a), a particle-free share of liquid comes out of the area to be found outside the membranes as a result of the pore size of the membranes. This liquid (T) passes part B of device AB, which contains particles enabling a specific adsorption of dissolved substances (details, see FIG. 1a). Via the three-directional valve (V2), which is in the ⊣∥ position, and the three-directional valve (V3), which is in the ⊩ position, the cleansed liquid (T) and the particle concentrate (K) are united. In the outcome of the process, the original liquid (F) is freed of dissolved, undesired component parts.

The treatment can be discontinuous and also continuous.

FIG. 1a—Adsorption—Details
The pores of membrane (a) only allow the liquid share (F) to pass as a result of their size. This share is freed of undesired, soluble component parts by the adsorber particles (B) and then leaves the adsorber. As a result of the switching of the three-directional valves (V2) and (V3) to match the process, the unification with the particle concentrate (K) occurring on the throughflow can be achieved.

FIG. 2: Regeneration
The filter is regenerated by a suitable washing solution being conveyed in a direction opposite to the working direction of the filter.

The washing solution (Reg) conveyed by the pump (P3) enters adsorber area B via the three-directional valve (V2). This is where the regeneration of the adsorber particles takes place. After this, the liquid (Reg) scavenges the hollow fibres (a) against the direction of separation and thus restores the original output (details, see FIG. 2a). After this, the medium loaded with contaminations (W) leaves the adsorber via the three-directional valve (V1), which is in the ⫟ position, without contact to the liquid to be cleaned. A contamination of the liquid (F) in the reservoir is prevented by the ⫟ position of the valve (V3).

FIG. 2a: Regeneration—Details
The adsorber module has to be regenerated for repeated use. For this, a suitable liquid (Reg) is guided into the adsorber via the valve (V2) against the normal direction of work. In the $1^{st}$ phase, there is the desorptive reactivation of the adsorber particles. After this, the membrane (a) is flowed through in the wrong direction and freed of deposits in or on the pores. Filtration and adsorption output of the adsorber module are restored. The switching of the three-directional valves (V1-3) to match the process prevents contamination of the stock of liquid with (Reg) or (W).

Figure 3:
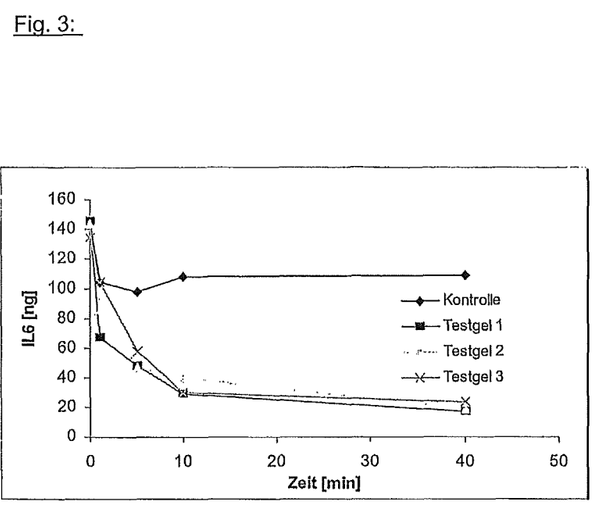

FIG. 3: Adsorption of IL6 in the Batch Experiment
n=3 (total volume: 0.1 ml, coupling density: 5 mg IgY/ml gel, medium: 2 ml heparinised, human full blood, antigen spike: 146 mg IL6, test: IL6-ELISA kit)

The invention claimed is:

1. A filter system for membrane-separated and adsorptive treatment of a liquid containing at least one target substance to be filtered, comprising a housing having an upper end, a lower end, an inlet opening at said upper end of said housing, at least a first three-directional valve connected outside said housing to said inlet opening, an outlet opening at said lower end of said housing, at least a second three-directional valve connected outside said housing to said outlet opening, a side opening in said housing between said upper end and said lower end, and at least a third three-directional valve connected outside said housing to said side opening, said housing containing a plurality of hollow fibre membranes with pores, said hollow fibre membranes arranged so as to form a reaction vessel inside said housing but not touching said housing, resulting in creation of an intra-luminal area inside said reaction vessel and an extra-luminal area between the hollow fibre membranes and said housing, said extra-luminal area capable of being filled with at least one adsorber material, with said hollow fibre membranes arranged in such a way that said inlet opening at said upper end of said housing opens into said reaction vessel, and at the bottom of said reaction vessel a screen, said screen creating a liquid area between said lower end of said housing and said screen, with said side opening in said housing being located below said screen and above said lower end, being arranged in such a way that regeneration of said adsorber material by reverse fluid flow is possible.

2. A filter system according to claim 1, wherein the filter system comprises at least one housing and at least one reaction vessel.

3. A filter system according to claim 1, wherein the extra-luminal area holds at least one adsorber material comprised of components.

4. A filter system according to claim 3, wherein the diameter of the components of the adsorber material is larger than the pore diameter of the hollow fibre membranes.

5. A filter system according to claim 4, wherein the adsorber material used therein has been functionalised.

6. A filter system according to claim 5, wherein proteins which specifically bind a target substance are used for the specific functionalisation.

7. A filter system according to claim 1, wherein the extra-luminal area comes into direct contact with the adsorber material and at least one target substance is bound to the adsorber material.

8. A filter system according to claim 1, wherein the extra-luminal area depleted of at least one target substance is combined with the intra-luminal area via the second three-directional valve connected to the outlet opening and/or the third three-directional valve connected to the side opening.

9. A filter system according to claim 1, wherein said regeneration occurs through the introduction of a cleansing liquid into the extra-luminal area by way of the side opening, said cleansing liquid removing at least one target substance from the adsorber material, and the extraction of the cleansing liquid and at least one target substance from the inlet opening via the first three-directional valve connected to the inlet opening.

* * * * *